(12) United States Patent
Heckele et al.

(10) Patent No.: US 6,830,574 B2
(45) Date of Patent: Dec. 14, 2004

(54) SURGICAL INSTRUMENT FOR APPLYING IMPLANTS

(75) Inventors: Helmut Heckele, Knittlingen (DE); Friedrich Hähnle, Bretten (DE); Eberhard Körner, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 189 days.

(21) Appl. No.: 09/802,639

(22) Filed: Mar. 9, 2001

(65) Prior Publication Data

US 2001/0021853 A1 Sep. 13, 2001

(30) Foreign Application Priority Data

Mar. 10, 2000 (DE) .......................................... 100 11 678

(51) Int. Cl.⁷ ................................................. A61F 2/38
(52) U.S. Cl. ......................................... 606/104; 606/86
(58) Field of Search ........................................ 606/104

(56) References Cited

U.S. PATENT DOCUMENTS

| | | | | |
|---|---|---|---|---|
| 2,248,054 A | * | 7/1941 | Becker | 145/52 |
| 5,100,417 A | * | 3/1992 | Cerier et al. | 606/139 |
| 5,329,834 A | | 7/1994 | Wong | |
| 5,354,292 A | * | 10/1994 | Braeuer et al. | 606/1 |
| 5,667,513 A | * | 9/1997 | Torrie et al. | 606/104 |
| 5,683,401 A | * | 11/1997 | Schmieding et al. | 606/104 |
| 5,690,676 A | * | 11/1997 | DiPoto et al. | 606/232 |
| 5,749,878 A | * | 5/1998 | Bracy et al. | 606/104 |
| 5,797,918 A | * | 8/1998 | McGuire et al. | 606/104 |
| 5,885,299 A | | 3/1999 | Winslow et al. | |
| 5,904,689 A | | 5/1999 | Jonjic | |
| 6,402,759 B1 | * | 6/2002 | Strong et al. | 606/104 |
| 6,436,100 B1 | * | 8/2002 | Berger | 606/73 |
| 6,440,136 B1 | * | 8/2002 | Gambale et al. | 606/73 |

FOREIGN PATENT DOCUMENTS

FR      2 764 795 A1    12/1998

* cited by examiner

Primary Examiner—Henry Bennett
Assistant Examiner—Nihir Patel
(74) Attorney, Agent, or Firm—Akin Gump Strauss Hauer & Feld LLP

(57) ABSTRACT

The instrument serves for the application in particular of bone grafts in the space between two vertebrae and includes a shank, a handle, and a holder for the implant, which forms the distal instrument part. The holder is pivotably mounted relative to the shank and can be fixed in any respective position which is reached by pivoting.

10 Claims, 3 Drawing Sheets

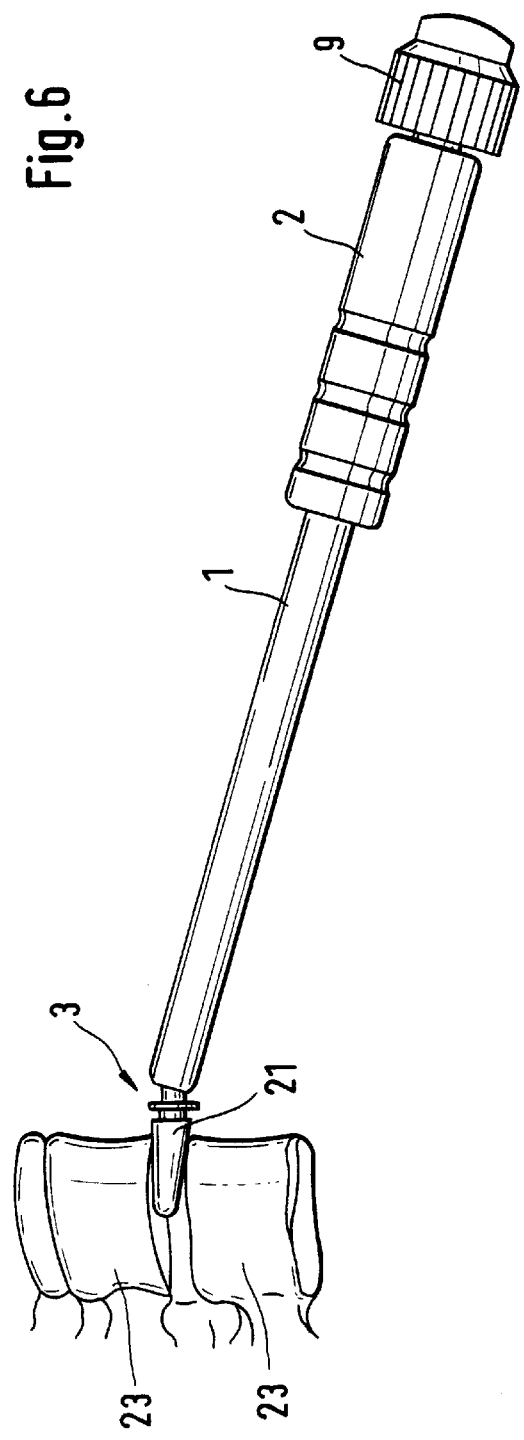
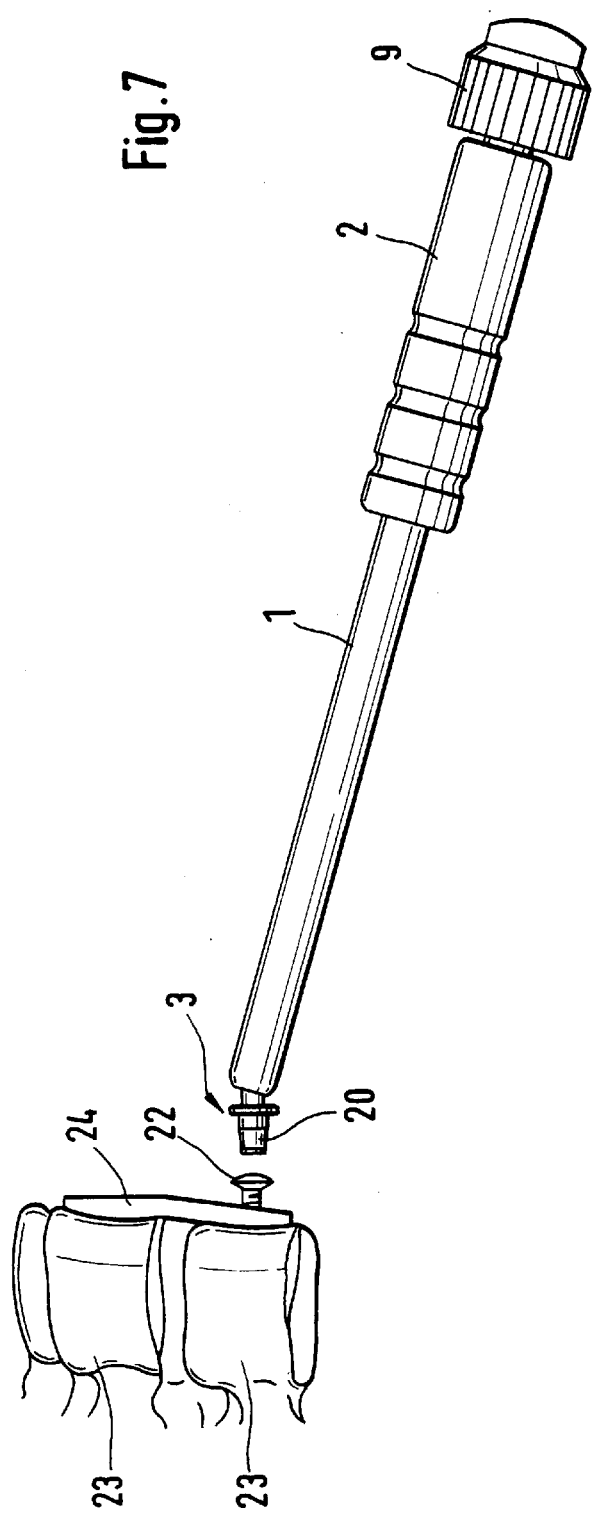

SURGICAL INSTRUMENT FOR APPLYING IMPLANTS

BACKGROUND OF THE INVENTION

The invention proceeds from a surgical instrument for applying implants, in particular bone grafts in the region of the vertebral column, consisting of a shank, a handle and a holder for the implant, which forms the distal instrument part.

With known instruments of this type, for example, the holder for the implant, which is formed as a spike, is rigidly connected to the shank of the instrument, i.e., in an unchangeable alignment to the instrument longitudinal axis. This is also the case with the instrument which is disclosed in FR-A 2 764 795 and described as a key, with which a support body may be implanted between neighboring vertebral bodies and with which the holder is formed as a threaded stem to which the implant is connected by screwing.

With the use of these surgical instruments it is necessary for the location of the defect concerned and the access thereto to lie in the axis direction of the instrument for the purpose of introducing the implant, which makes its application more difficult and demands an exact alignment of the instrument onto the location of operation.

BRIEF SUMMARY OF THE INVENTION

It is the object of the invention to specify a surgical instrument for applying implants, which permits a variably adjustable alignment of the implant in relation to the instrument and operation location, and specifically where required also even during the operation procedure. Furthermore, at the same time the instrument is to permit a simple and secure handling and with regard to the demands on hygiene able to be easily disassembled.

Proceeding from an instrument of the initially mentioned type, this object is achieved according to the invention in that the holder is pivotably mounted relative to the shank and is fixable in its position which is in each case achieved by pivoting.

According to a preferred embodiment of the invention, on the holder there may be provided an essentially spherical bearing body, which is mounted in the shank and which is pivotable about two axes intersecting perpendicularly, and which by way of a rod which runs through the shank and which with its distal end is movable against the periphery of the bearing body, may be fixed by way of clamping.

In order to achieve a rotational fit connection between a handle of the instrument and the bearing body, the bearing body may be provided with a groove running on a circular path of more than 180°, wherein into the groove engage pins which are fastened to the shank, which lie on the same axis and which form a first pivot axis for the bearing body, and the bearing body with the pins sliding in the groove is pivotable about a second pivot axis which stands perpendicular to the first pivot axis and the plane of the groove.

The fixing of the bearing body by clamping may usefully be made possible in that the distal open end of the shank is drawn inwards and forms a spherically curved annular surface as a shoulder and bearing surface for the bearing body, and that in the distal end region of the rod formed as a tube there is provided an insert whose end projecting out of the rod is formed as a spherically curved annular surface, which by way of distal adjustment of the rod can be brought to bear against the periphery of the bearing body, in order to fix this bearing body and thus also the holder carrying the implant in the respective pivot position by way of a clamping effect.

In the proximal end region of the handle, rigidly connected to the shank, there is provided an inner thread into which a threaded projection of a clamping head is screwed, said head being rigidly connected to the rod. By rotating the clamping head and thus the rod in a first direction, this may be distally adjusted for fixing the bearing body, and reversely by rotating in a second direction may be adjusted proximally, in order thus to lift the clamping effect between the bearing body and the parts engaging it or only to reduce this clamping effect somewhat. The holder thus becomes pivotable and subsequently, after pivoting into a suitable position, may again be fixed by rotating the clamping head in the first direction.

The holder on the proximal side blends into an annular shoulder, forming an abutment for the implant, and via a cylinder projecting through the open end of the shank is rigidly connected to the bearing body. If with the instrument, bone parts or bone grafts are to be applied, it is useful to form the holder as a distally, conically tapering, threaded spike, which may be simply screwed into the implant and which securely holds it.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 6 shows the instrument according to the invention in an application as a bone graft applicator; and FIG. 7 shows the instrument according to the invention in an application as a screwdriver.

DETAILED DESCRIPTION OF THE INVENTION

Figure 1:
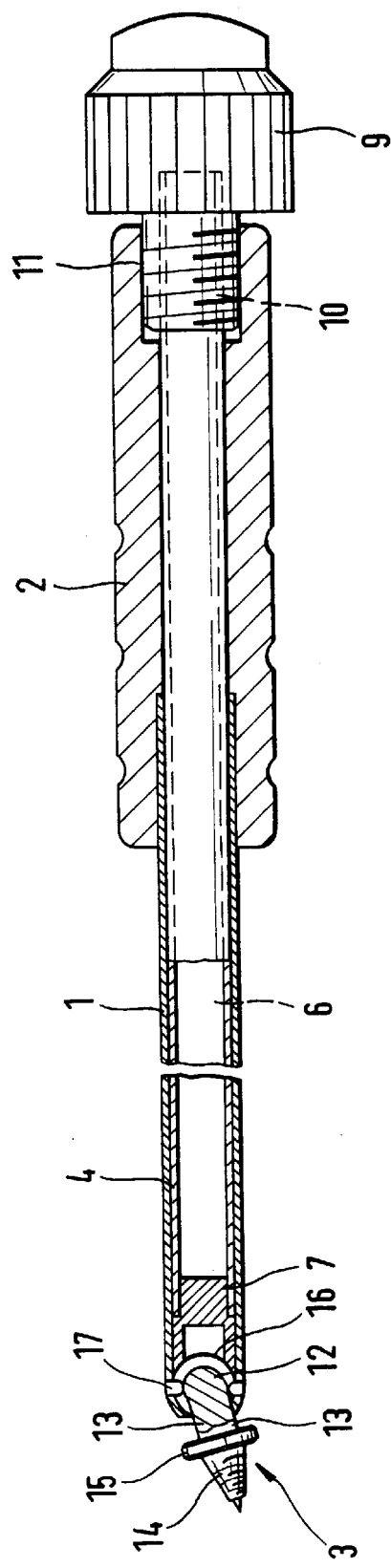
FIG. 1 is a total view of the instrument according to the invention in a part longitudinal section.

The instrument consists according to FIG. 1 of a shank 1 with a handle 2 arranged proximally on the shank, of a holder 3 for the implant, which is arranged on the distal end of the shank, and of an actuation rod 4.

Figure 2:
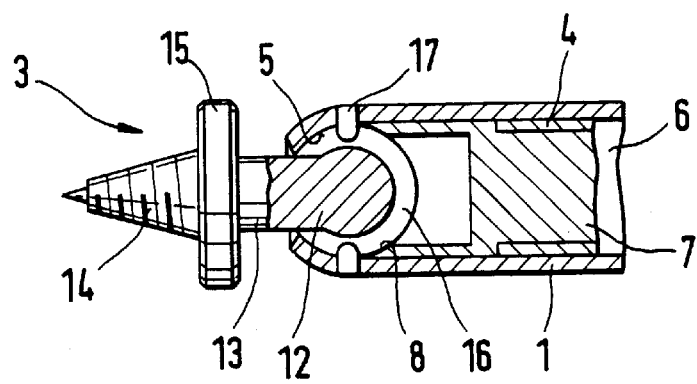
FIG. 2 is an enlarged sectional representation of the distal end region of the instrument shown in FIG. 1.
Figure 3:
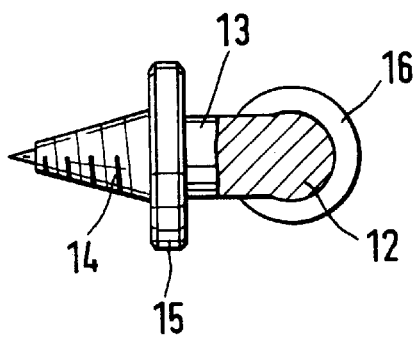
FIG. 3 shows the bearing body and holder of the instrument according to FIG. 2.
Figure 4:
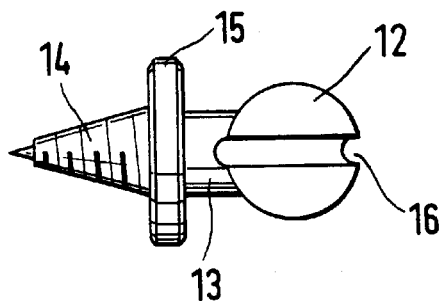
FIG. 4 shows the bearing body and holder of the instrument according to FIG. 2 in a plan view.
Figure 5:
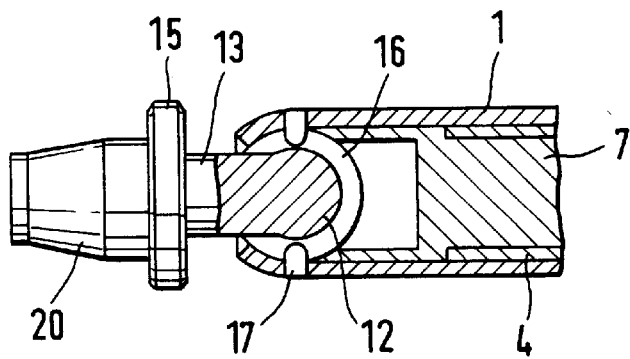
FIG. 5 is a sectional representation according to FIG. 2 with a holder formed as a screwdriver tip.

The shank 1 is formed tubular and comprises at its distal end an annular surface 5 whose contour is shaped spherically (see FIG. 2), but may also be shaped conically. The shank 1 and the handle 2 are non-releasably connected to one another. In a channel 6 of the shank an actuation rod 4 is arranged in an axially displaceable manner. This is provided at its distal end with an insert 7 whose end-face region comprises a spherical recess 8. On the proximal end of the actuation rod 4 there is seated a clamping head 9 with a threaded projection, which is screwed into a corresponding inner thread 11 on the proximal end of the handle 2. Thus, by rotating the clamping head 9 in a first direction, the actuation rod 4 with the insert 7 are moved distally, and by rotating the clamping head in another second direction, the rod 4 and insert 7 are moved proximally.

At the distal-side end of the shank 1 there is mounted the holder 3. This is provided with an essentially spherical bearing body 12 which, via a cylindrical extension 13, blends into a distally tapering, conical, threaded spike, at whose foot there is provided an annular shoulder 15 as an abutment for the implant. The bearing body 12 is provided with a groove 16 which runs on a circular path of more than 180°, into which engage pins 17 fastened on the shank 1 and lying on the same axis.

For preparing the instrument for an operation the holder 3 is first assembled. The holder may for this purpose be designed as two parts and comprise a threaded projection between the bearing body 12 and the threaded spike 14, to which these two parts may be releasably connected. The application of the holder 3 is then effected such that the bearing body 12 with the cylindrical extension 13 in front is first introduced into the channel 6. Then, the actuation rod 4 is pushed from the proximal end into the channel. By way of the mentioned threaded connection 10/11 of the insert 7 located at the end of the actuation rod 4, and by rotating the clamping head 9 in the first direction, the rod 4 comes to take its bearing. Thus, the bearing body 12 is clamped between the annular surface 5 and the recess 8, so that subsequently the threaded spike 14 may be screwed to the bearing body 12.

The receiving, for example, of an implant 21 to be applied between two vertebral bodies 23 (FIG. 6) is effected such that the conical, threaded spike 14 is screwed into the implant up to its bearing on the annular shoulder 15. Thereafter, by proximal adjustment of the actuation rod 4, the clamping force acting on the bearing body 12 may be reduced or lifted, so that the desired position of the holder and thus also of the implant relative to the instrument axis may be set. After fixing this position again by distal adjustment of the actuation rod 4, the implant under endoscopic observation may now be brought to the location of the defect and applied. With this there exists the possibility of a correction of the previously set position within the context of a self-alignment, specifically by way of an intermediate release of the holder, and subsequent fixing of the holder as soon as this has automatically aligned into a position suitable for the application procedure.

In order, for example, to connect and bridge neighboring vertebral bodies by way of a bone plate 24, according to FIG. 7, which is to be screwed to these bodies, instead of the threaded spike 14 there is applied a holder 3 with a screwdriver tip 20, so that the instrument in total as a screwdriver, with the screws 22 as implant parts, may be screwed through the bone plate 24 into the respective vertebral bodies 23.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A surgical instrument for applying an implant, comprising a shank having a longitudinal axis, a handle connected proximally to the shank, and a holder for the implant, the holder forming a distal instrument part, wherein the holder is mounted to be pivotable about at least one axis perpendicular to the longitudinal axis of the shank and is fixable in any respective position achieved by pivoting.

2. The instrument according to claim 1, wherein the holder is provided with an essentially spherical bearing body which is mounted in the shank, the bearing body being pivotable about the at least one axis, and further comprising a rod which runs through the shank, a distal end of the rod being axially movable against a periphery of the bearing body, fixed to fix the bearing body by clamping.

3. The instrument according to claim 2, wherein the bearing body is provided with a groove running on a circular path of more than 180°, wherein the shank is provided with pins which engage into the groove, the pins lying on a common axis and forming a first pivot axis for the bearing body, and wherein the bearing body with the pins sliding in the groove is pivotable about a second pivot axis which stands perpendicular to the first pivot axis and a plane of the groove.

4. The instrument according to claim 2, wherein a distal open end of the shank is drawn inward and forms a spherically curved annular surface as a shoulder and bearing surface for the bearing body.

5. The instrument according to claim 2, wherein a distal end region of the rod is formed as a tube in which is provided an insert whose end projecting out of the rod is formed as a spherically curved annular surface, which can be brought to bear against a periphery of the bearing body by adjustment of the rod in a distal direction.

6. The instrument according to claim 2, wherein the handle is rigidly connected to the shank and has a proximal end region with an inner thread, into which inner thread a threaded projection of a clamping head is screwed, said clamping head being rigidly connected to the rod.

7. The instrument according to claim 2, wherein the holder on its proximal end transitions into an annular shoulder and is rigidly connected to the bearing body via a cylindrical extension projecting through an open end of the shank.

8. The instrument according to claim 1, wherein the implant comprises a bone graft in a region of a vertebral column.

9. The instrument according to claim 2, wherein the bearing body is pivotable about two axes which intersect perpendicularly.

10. The instrument according to claim 1, wherein the holder comprises a screwdriver tip.

* * * * *